United States Patent [19]
Dreessen et al.

[11] Patent Number: 5,843,150
[45] Date of Patent: Dec. 1, 1998

[54] SYSTEM AND METHOD FOR PROVIDING ELECTRICAL AND/OR FLUID TREATMENT WITHIN A PATIENT'S BRAIN

[75] Inventors: Chrit W. Dreessen, Stein; Paulus A. A. Gubbels, Brunssum; Paulus G. Adams, Munstergeleen; Victor P. J. Duysens, Grevenbicht, all of Netherlands

[73] Assignee: Medtronic, Inc., Minneapolis, Minn.

[21] Appl. No.: 947,107

[22] Filed: Oct. 8, 1997

[51] Int. Cl.$^6$ ........................................................ A61N 1/02
[52] U.S. Cl. ............................ 607/116; 128/898; 600/378; 604/175
[58] Field of Search ............................ 607/57, 116, 137; 128/897, 898, 899; 600/378; 604/268, 278, 175, 93; 606/130

[56] References Cited

U.S. PATENT DOCUMENTS

| | | | |
|---|---|---|---|
| 3,663,965 | 5/1972 | Lee, Jr. et al. | 3/1 |
| 3,995,644 | 12/1976 | Parsons | 128/418 |
| 4,245,645 | 1/1981 | Arseneault et al. | 128/642 |
| 4,328,813 | 5/1982 | Ray | 128/791 |
| 5,464,446 | 11/1995 | Dreessen et al. | 128/642 |

*Primary Examiner*—William E. Kamm
*Attorney, Agent, or Firm*—Michael J. Jaro; Harold Patton

[57] ABSTRACT

A system and method for providing electrical and/or fluid treatment within a patient's brain, the system and method utilizing a feedthrough assembly made of a compressible material, and a disk-like pinch-on part, or resilient clamping part, which is secured around the feedthrough assembly to provide radially inward compressive force to reliably fix the lead after it has been positioned relative to the patient's skull. The feedthrough assembly is suitably made of a compressible biocompatible material such as silicone rubber, and has a annular receiving groove which is located so that it is accessible above the cranium after the feedthrough assembly is fixed within a burr hole in the patient's head. The pinch-on part, or clamping means is manufactured in a normally closed position, but can be opened, as by use of a forceps-type instrument, for positioning around the assembly annular groove. The anchored lead or catheter member is operatively connected to an implantable pulse generator or fluid pump, or both, to provide a system for treatment within the patient's brain.

20 Claims, 3 Drawing Sheets

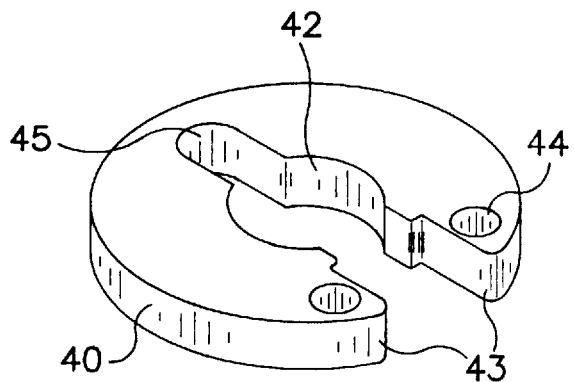
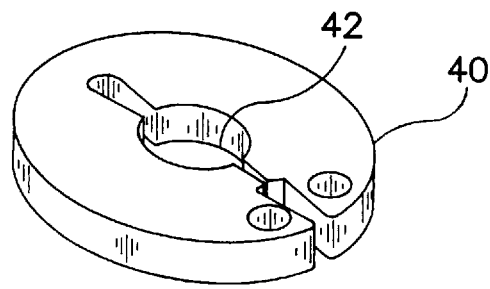
FIG. 2A  FIG. 2B
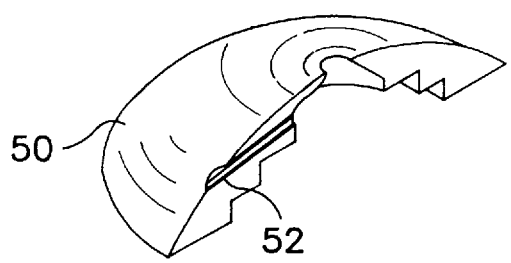
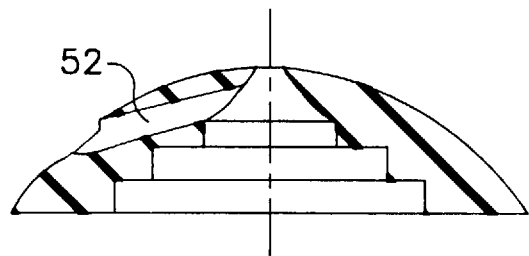
FIG. 3B  FIG. 3A
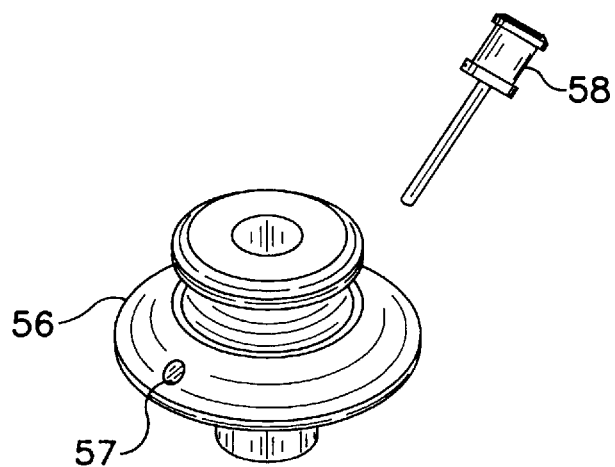
FIG. 4

SYSTEM AND METHOD FOR PROVIDING ELECTRICAL AND/OR FLUID TREATMENT WITHIN A PATIENT'S BRAIN

FIELD OF THE INVENTION

This invention relates to a system and method for providing electrical and/or fluid treatment within a patient's brain, the system and method featuring a cranial burr hole connector subsystem, whereby the cranial burr hole connector subsystem anchors a brain treatment lead or catheter and thereby fixes the lead or catheter in position with respect to the patient's brain.

BACKGROUND OF THE INVENTION

Systems for providing either electrical stimulation of the brain or coupling fluid to or from the brain are coming into increased use for various purposes. Electrical stimulation of the brain is utilized for relief of chronic pain and treatment of movement disorders. A typical electrical brain stimulation system comprises a pulse generator operatively connected to the brain by a lead. The lead has one or more electrodes at its distal end, designed to be implanted within the patient's brain at a precise location, so that the electrode or electrodes are optimally and safely positioned for the desired stimulation. The lead is connected to the pulse generator at its proximal end, and also needs to be anchored with respect to a burr hole drilled in the patient's skull or cranium, in order to reliably secure the distal end which carries the electrodes. Likewise, in the case of a catheter for providing fluid to the brain or for providing drainage, it is necessary to be able to secure the distal portion of the catheter that passes through the skull and transfers the fluid at a predetermined exact location within the brain. Still further, for a combined catheter and lead member, such secure and reliable anchoring of the member so that the distal end is precisely located within the skull, is very important. As used herein, the term lead member, or lead-type member, refers to any such cranial catheter or lead.

Reference is made to U.S. Pat. No. 5,464,446, "Brain Lead Anchoring System," assigned to Medtronic, Inc., which is incorporated herein by reference. The referenced patent illustrates an effective lead anchoring system, and it discusses the method of providing access through the skull by drilling a burr hole with a cranial drill, inserting a stimulation lead through the burr hole and positioning it so that the electrode or electrodes are at the desired stimulation site. The lead is positioned using a stereotactic instrument, which permits a very precise movement within the brain. Once the lead is positioned and tested to determine that the results of stimulation are satisfactory, it is critical that the lead is not moved, since even the slightest displacement can result in less than optimal results, and even injury to the brain.

The referenced anchoring system shows a basic anchor for fixing the lead in place with the distal portion extended through the cranial burr hole, and then securing it by bending it into a slit such that it is held by a friction fit. However, this system does not provide a reliable way for accurately securing the lead, or catheter, before it is bent into the fixation position. Thus, such a system does not provide against small movement of the distal end of the lead at the time of fixating, or securing the lead in place. What is required, and what has remained a substantial need in the art, is a system and method for accurately placing a cranial lead directly through the skull burr hole and which enables securing of the lead or catheter precisely in position relative to the brain before it is connected either to a stimulator or fluid source.

Another system for fixing a cranial lead is disclosed in U.S. Pat. No. 4,328,813. This patent discloses a socket and plug anchoring system wherein the lead is engaged by and held within a neck portion of the socket and recessed portion of the plug. However, in this arrangement the lead may easily be moved, particularly axially, when the plug is forced into engagement with the socket.

In U.S. application Ser. No. 08/705,566, filed Aug. 29, 1996, assigned to the same assignee as this invention and incorporated herein by reference, there is shown an apparatus and method wherein a compression screw cap is screwed down onto a compressible seal, the seal being flexible and compressed laterally against the outer wall of the lead member. While this provides a substantial improvement over the prior art, it entails a multiple component structure which can be difficult to implant. There remains a need in the art for a simpler system which reliably engages the lead substantially circumferentially, so as to minimize any possible displacement at the time of fixation within the cranial burr hole.

SUMMARY OF THE INVENTION

There is provided a system and method for providing electrical and/or fluid treatment within a patient's brain, having a subsystem for anchoring a lead-type member within a cranial burr hole in a patient, the anchoring subsystem having a feedthrough assembly made of a compressible material, e.g., silicone rubber. The feedthrough assembly has an axial opening for receiving the lead-type member, and is sutured or otherwise fixed to the inner walls of the burr hole. The feedthrough assembly has an inwardly extending annular groove which is above the patient's cranium after the feedthrough is fixed to the burr hole. A cooperating pinch-on part, made of a resilient material, is pinched into place around the receiving groove by first stretching it to a stretched state for placement around the groove, and then permitting the part to relax so that it returns to its normally biased state and compresses the feedthrough assembly radially inward around the annular groove. This compression forces the feedthrough assembly tightly against the lead-type member and holds it in a fixed position relative to the feedthrough assembly, and thus relative to the patient burr hole. The pinch-on part is preferably made of CrNi, or titanium, and is fabricated to be normally in a closed position, whereby it effectively wraps around the feedthrough assembly and provides an inwardly compressive force. The pinch-on part is opened with forceps for positioning around the feedthrough, and when the forceps are removed, the pinch-on part immediately fastens the lead.

BRIEF DESCRIPTION OF THE DRAWINGS

FIG. 2A is a perspective view of the pinch-on part in an expanded, or open state, for mounting on to the feedthrough assembly; FIG. 2B is a perspective view of the pinch-on part in its normally closed state, as it is when it has been mounted on the feedthrough assembly.

FIG. 3A is a cross-sectional view of a burr hole head piece which is mounted over the feedthrough assembly after the lead-type member has been secured; FIG. 3B is a cutaway perspective view of the burr hole head piece.

FIG. 4 is a perspective of a drill-hole gauge and locking pin used for drilling suture holes in accurate positions relative to the suture hole openings in the feedthrough assembly.

It should be understood the drawings are not necessarily to scale.

DESCRIPTION OF THE PREFERRED EMBODIMENTS

Figure 1B:
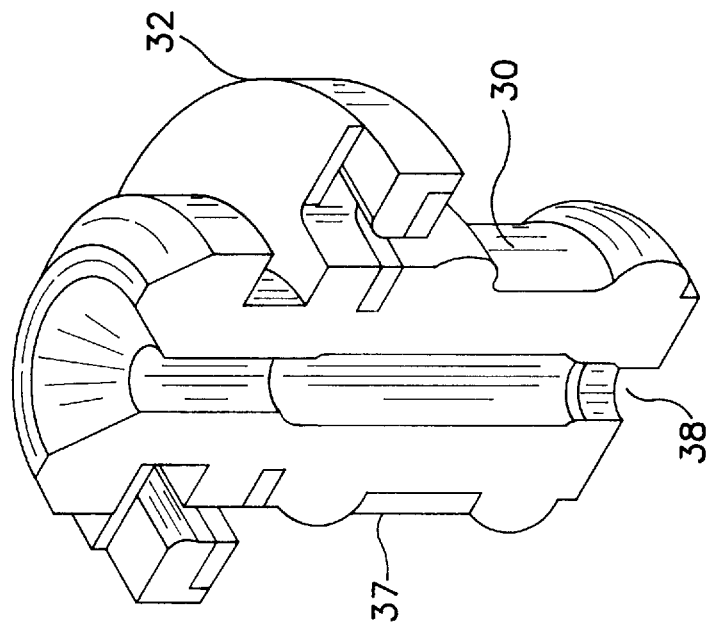
FIG. 1B is a perspective view of the feedthrough assembly shown in cross-section.
Figure 1A:
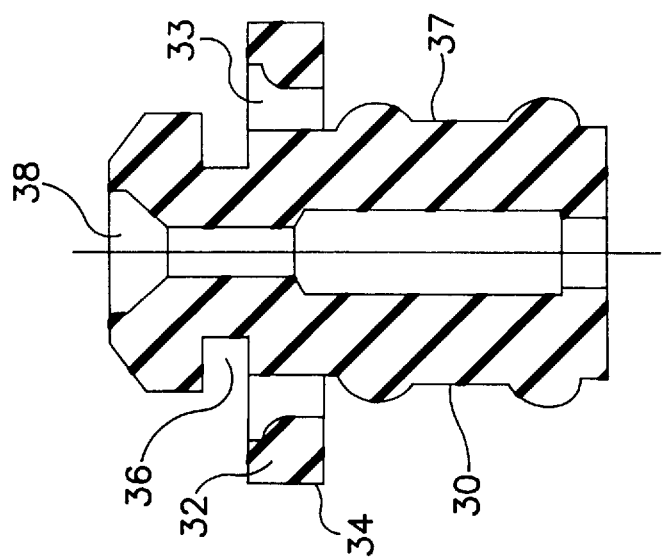
FIG. 1A is a cross-sectional view of the feedthrough assembly of this invention.

Referring now to FIGS. 1A and 1B, the primary component parts of the feedthrough assembly is shown, illustrating the primary component parts. The assembly piece 30 is preferably made of a biocompatible compressible material, such as silicone rubber. An upper flange 32 carries suture holes, or slots, spaced at about 180. Around the outside of the flange, i.e., to the outside of the suture holes, is a ring, or disk 34, suitably Dacron, which is vulcanized into the silicone rubber to provide strength to the outside of the ring with respect to the sutures which are to be applied. Above flange 32 is an annular recess, or groove 36, which has a outer dimension designed to receive the pinch-on part 40, as discussed further below. Below the flange 32, and around the portion of the assembly which resides against the cranial wall of the burr hole, is a metal ring 37, preferably CrNi., or titanium, to give extra strength so as to prevent compression of the feedthrough assembly caused by subsequent growth of skull tissue, which could cause dislocation of the lead. This is important, as a small movement due to such skull tissue growth could change the lead position enough so as to alter the electrode positions, and cause the lead to be substantially ineffective. Also illustrated is axial aperture 38, which extends the length of the assembly, for receiving the lead-type member.

Referring now to FIGS. 2A and 2B, the pinch-on part 40 is preferably made of Cr.Ni. or titanium, but may also be another type of biocompatible material, e.g., a plastic material. The pinch-on part is substantially disk-like in outer geometry, but has a slit 45 that extends from end points 43 a large portion of the diameter of the part. The slit provides an opening for expanding ends 43, so that it can be pressed on over the groove 36 of the feedthrough assembly. The slit also features an inner surface 42, which is configured so that it has a normal diameter which is effectively smaller than the diameter of groove 36, so that when part 40 returns to its normally biased closed position, it provides inwardly circumferential compressive force on assembly 30. As seen in FIG. 2B, in the closed position, the part 40 provides a small opening formed by surfaces 42, which results in the compressive force. Adjacent to the ends 43 there are provided holes 44, for receiving forceps which are used to open the part at the time of placement of the part around the feedthrough assembly; when the forceps are withdrawn the part immediately snaps back to its normal closed position.

Referring to FIGS. 3A and 3B, there are shown views of the head (or cap) which is fixed to the top of the assembly after the lead has been secured. The cap contains a slot 52 for channeling the lead laterally away from the assembly axis, in a known manner.

Figure 5A:
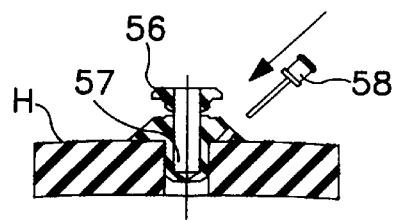
FIG. 5A is a diagrammatic view of a drill gauge positioned with respect to a cranial burr hold, with an indication of how a locking pin is placed in an already drilled suture hole.
Figure 5B:
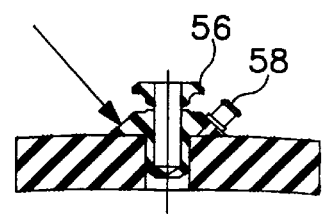
FIG. 5B is a diagrammatic view illustrating use of the drill gauge for drilling a second suture hole.

Referring now to FIGS. 4, 5A and 5B, the method of drilling suture holes into the cranium in accordance with this invention is illustrated. Drill gauge 56, having a pair of oppositely aligned side holes 57, is seated down into the burr hole drilled into the head H. A first suture hole is drilled through one of the gauge holes 57, and then the locking pin 58 is positioned through the hole 57 to secure the gauge 56 against rotation, as indicated in FIG. 5A. After this, the second burr hole is drilled through the opposing hole 57 in the gauge, as indicated. Although not shown in the drawings, in order to be certain that the shank of the gauge which enters into the burr hole properly fits the hole, with an acceptable tolerance, the shank can be provided with a groove filled with a compressible O-ring.

Figure 6:
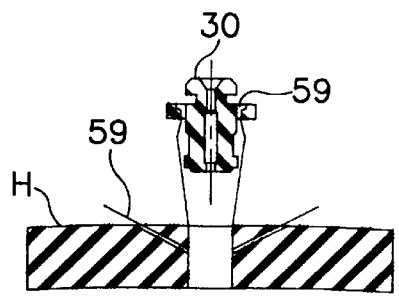
FIG. 6 is a diagrammatic view illustrating suturing of the feedthrough assembly to the patient's head.

Referring to FIG. 6, there is shown a diagram illustrating the suturing of assembly 30 into the head H. The sutures are threaded through the drilled holes and the slots 33, in a conventional manner well known in the art. Although FIG. 6 illustrates the assembly being sutured into place without the pinch-on part 40, the pinch-on 40 may be attached prior to suturing, as discussed further below.

Figure 7B:
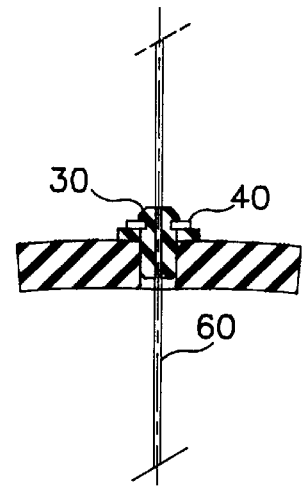
FIG. 7B is a diagrammatic view showing the pinch-on-part locked onto the feedthrough assembly.
Figure 7A:
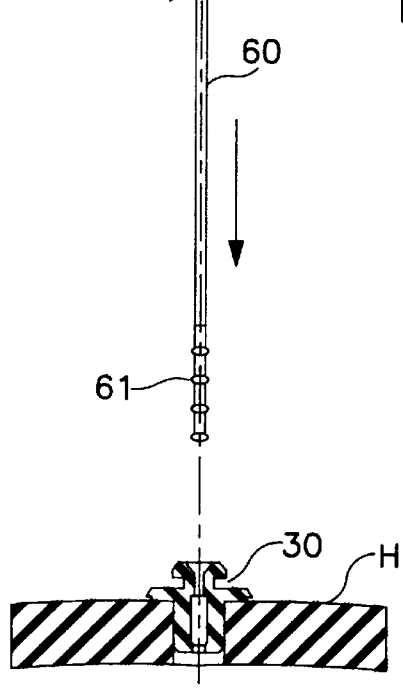
FIG. 7A is a diagrammatic view illustrating placement of a lead-type member through the feedthrough assembly.
Figure 8:
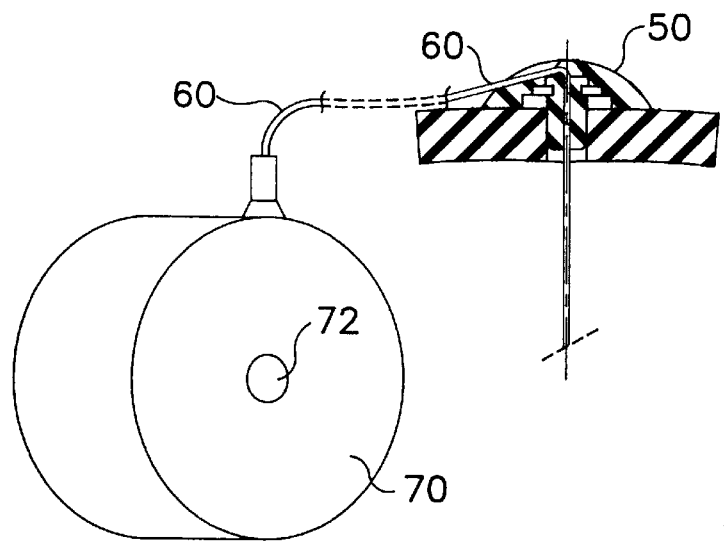
FIG. 8 is a diagrammatic view illustrating the system of this invention, showing the connector subsystem fully assembled with the lead member positioned through a slot in the cap, or head piece, and the lead member connected to a pulse generator or pump.

Referring now to FIG. 7A, there is illustrated the procedure of placing the lead member 60 axially through the assembly 30. The lead 60 may be a standard lead as used in the art for delivering electrical stimuli, in which case it has a conductor (not shown) connecting from the lead proximal end to each electrode at the lead distal end. Alternately, or in combination, the lead member may have a lumen running its length, with a port at its distal end, for delivering fluid to or from the brain area being treated. The technique of placing the lead such that the electrodes, illustrated at 61, are optimally positioned within the patient's head, is a matter of known medical technique; a fluid delivery lead member is likewise positioned in accord with known procedures. After the lead member 60 is in place, the pinch-on part 40 is positioned around the receiving groove 36 of assembly 30, as discussed above; the resulting lead fixed to the assembly 30 by the pinch-on part 40 is illustrated in FIG. 7B. Following this, as shown in FIG. 8, the lead is positioned into cap 50 and through the slot, and cap 50 is secured over the feedthrough assembly and through the skull by conventional means.

As discussed above, the pinch-on part can be mounted on the feedthrough assembly either before or after the feedthrough is positioned into the skull. In the case where part 40 is positioned prior to fixing the feedthrough in the skull, when the physician proceeds to position the lead through the assembly, the forceps are used to expand part 40 while the lead is being positioned. When the lead is then accurately positioned, the forceps are released and part 40 fixes the lead in place. Note that depending upon the material used for part 40, the ends 43 can be provided with coupling means, such as a "swallow-tail," such that the fork ends 43 lock into each other. Although the system and method of this invention has been illustrated with the drawing of only two suture holes, it is to be understood that three or more suture holes can be utilized, with a corresponding number of slots 33 provided in assembly 30, and holes 57 provided in gauge 56.

Referring again to FIG. 8, the anchored lead member 60 is illustrated as connected to an implantable device illustrated at 70. Device 70 may be a pulse generator for delivering stimulus pulses, in which case lead 60 has one or more electrodes at its distal end, with respective conductors connecting from the lead proximal end to each electrode. Alternately, device 70 may be a pump, such as the Medtronic SynchroMed pump; or both stimuli and fluid delivery can be used. For a system having a pump for delivering a fluid, a reservoir filling port is provided, as indicated at 72; lead member 60 has a fluid delivery system in the form of a lumen running the length of the member, and a fluid port at about the distal end. Thus, the invention provides a system for providing electrical and/or fluid treatment within the brain, characterized by an anchoring subsystem for anchoring the lead member with respect to a patient's skull.

It is to be understood, the term "lead" is used herein in its broadest sense and includes any stimulation lead or sensing lead, a combination thereof or any other elongated member, such as a catheter, which may usefully be introduced into a body. In addition, although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A system for anchoring a lead-type member within a cranial burr hole in a patient, comprising:

a feedthrough assembly made of a compressible material, having an axial opening therethrough for receiving the member, a fixation portion for being fixedly positioned within the burr hole, and an annular receiving portion; and annular clamping means positioned around the receiving portion for compressing the assembly radially inward so as to fix the member relative to the assembly and thus with respect to the burr hole, the clamping means being made of a resilient material and normally biased so that when it engages the receiving portion it exerts a radially inward compressive force on the assembly at the receiving portion.

2. The system as described in claim 1, wherein the receiving portion comprises an inwardly extending circumferential groove having a first predetermined circumference, and the clamping means is moveable between a stretched state and a normal state and comprises an inner surface which engages the groove, the inner surface being substantially annular and having a circumference slightly less than the first circumference when in its normal state.

3. The system as described in claim 2, wherein the clamping means comprises means for facilitating stretching of the means to its stretched state for engaging the receiving portion.

4. The system as described in claim 3, wherein the clamping means comprises locking means for locking the clamping means around the receiving portion.

5. The system as described in claim 1, wherein the feedthrough assembly is made of silicone rubber and comprises suture holes for enabling suturing of the assembly to the patient's skull.

6. The system as described in claim 1, comprising strengthening means around the suture holes to prevent breaking of the suture holes.

7. The system as described in claim 6, wherein the strengthening means comprises a DACRON ring.

8. The system as described in claim 1, wherein the fixation portion comprises a ring of highly compression-resistant material.

9. The system as described in claim 1, further comprising a cap for positioned over the feedthrough assembly, the cap having a slot for providing a lateral pathway for the lead-like member.

10. A method of reliably fixing a cranial lead member with respect to a patient's skull, comprising:

preparing a burr hole in the patient's skull;

providing a compressible feedthrough assembly having an axial aperture for receiving the member, and inserting the assembly into and fixing it within the burr hole;

inserting the lead member axially through the assembly, and determining a proper axial location of the lead; and engaging a resilient pinch-on part around the assembly to compress the assembly radially inward so as to engage the member while it is at the proper axial location.

11. The method as described in claim 10, wherein the pinch-on part is moveable from a normal closed state to an open state, and wherein the engaging step comprises moving the part to its open state and positioning it around the assembly, and then releasing the part to return to its closed state.

12. The method as described in claim 10, comprising engaging the part around the assembly after inserting the lead member axially through the assembly.

13. The method as described in claim 10, comprising first engaging the part around the assembly, then inserting the assembly into and fixing it within the burr hole, then expanding the part to its open state and inserting the lead member through the assembly, and releasing the part to its closed state after determining the proper lead member location.

14. The method as described in claim 10, comprising expanding the part with forceps in order to first position it around the assembly, and then releasing the part so that it snaps into its closed state around the assembly.

15. The method as described in claim 10, wherein the fixing comprises the step of suturing the assembly to the patient's skull.

16. The method as described in claim 15, wherein the suturing comprises the step of drilling a pair of suture holes into the patient's skull.

17. The method as described in claim 16, wherein the suturing comprises placing a suture hole gauge element in the burr hole for providing the location of the suture holes.

18. A system providing treatment within a patient's brain, the system comprising a lead member, the lead having a proximal and distal ends, a device connected to the lead proximal end for delivering fluid or electrical stimuli to the lead, the lead having delivery means for delivering fluid or electrical stimuli through its distal end to an area within the patient's brain, and anchoring means for anchoring the lead member within a cranial burr hole in the patient's skull, the anchoring means further comprising:

a feedthrough assembly made of a compressible material, having an axial opening therethrough for receiving the member, a fixation portion for being fixedly positioned within the burr hole, and an annular receiving portion; and annular clamping means positioned around the receiving portion for compressing the assembly radially inward so as to fix the member relative to the assembly and thus with respect to the burr hole, the clamping means being made of a resilient material and normally biased so that when it engages the receiving portion it exerts a radially inward compressive force on the assembly at the receiving portion.

19. The system as described in claim 18, wherein the delivery means comprises at least one electrode at about the lead member distal end and at least one conductor for delivering stimuli from the lead member proximal end to the at least one conductor, and the implantable device has stimulus generator means for delivering stimuli to the lead member proximal end.

20. The system as described in claim 18, wherein the delivery means comprises a lumen running from the lead member proximal end to the lead member distal end, and the device comprises pump means for delivering a fluid to the lead member for delivery to the area within the patient's brain.

* * * * *